(12) United States Patent
Yu et al.

(10) Patent No.: US 11,844,529 B2
(45) Date of Patent: Dec. 19, 2023

(54) HEMOSTATIC CLIP

(71) Applicant: Beijing Donglin Fushi Medical Devices Co., Ltd., Beijing (CN)

(72) Inventors: Ling Yu, Beijing (CN); Chun Yu, Beijing (CN)

(73) Assignee: BEIJING DONGLIN FUSHI MEDICAL DEVICES CO., LTD., Beijing (CN)

( * ) Notice: Subject to any disclaimer, the term of this patent is extended or adjusted under 35 U.S.C. 154(b) by 70 days.

(21) Appl. No.: 17/519,516

(22) Filed: Nov. 4, 2021

(65) Prior Publication Data

US 2022/0133326 A1 May 5, 2022

(30) Foreign Application Priority Data

Nov. 5, 2020 (CN) .......................... 202022529609.1
Feb. 7, 2021 (CN) .......................... 202110177027.8
Feb. 7, 2021 (CN) .......................... 202120360522.8

(51) Int. Cl.
*A61B 17/122* (2006.01)
*A61B 17/12* (2006.01)

(52) U.S. Cl.
CPC .. *A61B 17/122* (2013.01); *A61B 2017/12004* (2013.01)

(58) Field of Classification Search
CPC ..... A61B 17/10; A61B 17/122; A61B 17/128; A61B 17/1285; A61B 17/1227; A61B 2017/294; A61B 2017/2931; A61B 2017/12004
See application file for complete search history.

(56) References Cited

U.S. PATENT DOCUMENTS

| 6,358,267 | B1* | 3/2002 | Murakami | ............. | A61B 17/29 606/205 |
| 2009/0206131 | A1* | 8/2009 | Weisenburgh, II | .......................... A61B 17/3209 227/180.1 |
| 2018/0153552 | A1* | 6/2018 | King | .................... A61B 17/128 |

FOREIGN PATENT DOCUMENTS

CN 211049500 U 7/2020

\* cited by examiner

*Primary Examiner* — Shaun L David
*Assistant Examiner* — Rachael L Geiger
(74) *Attorney, Agent, or Firm* — Ladas & Parry, LLP

(57) ABSTRACT

The present invention discloses a hemostatic clip, including an inner sleeve, a transitional inner sleeve, steel micro balls, a clip holder, a ball head pull rod, and clamps. The ball head pull rod is accommodated in the transitional inner sleeve, the transitional inner sleeve is accommodated in the inner sleeve, the inner sleeve is limited between the transitional inner sleeve and the clip holder, the steel micro balls are clamped between the clip holder and the transitional inner sleeve, and the steel micro balls are fixed to the clip holder. By pulling the ball head pull rod, the transitional inner sleeve is driven to move backward, so that a front end of the transitional inner sleeve is elastically deformed, to separate the transitional inner sleeve from the steel micro balls and the clip holder.

9 Claims, 10 Drawing Sheets

HEMOSTATIC CLIP

TECHNICAL FIELD

The present invention relates to a hemostatic clip and belongs to the technical field of medical instruments.

BACKGROUND

In a surgery, the use of a hemostatic clip is one of widely applied hemostatic methods. The hemostatic clip can be used to effectively stop bleeding and prevent rebleeding, reduce adverse reactions, and greatly improve safety and cure rate of an endoscopic treatment of gastrointestinal bleeding. A hemostatic mechanism of a hemostatic clip is the same as that of surgical blood vessel ligation or suturing, and is essentially a physical-mechanical method in which a mechanical force generated when the hemostatic clip closes is used to ligate surrounding tissues and bleeding blood vessels together, to close the bleeding blood vessels to block a blood flow to stop bleeding. The hemostatic clip is applicable to a hemostasis treatment of non-varices active bleeding and visible vascular stump lesions.

In the previous patent application "HEMOSTATIC CLIP" (CN211049500U) of the applicants, a hemostatic clip is disclosed, which implements opening and closing of two clip arms by using a ball head pull rod, and implements separation of a clamping part at a front end and a control part at a rear end of the hemostatic clip by using the ball head pull rod in cooperation with a plastic sleeve and a steel sleeve. The structure is connected by an interference fit, but since the clip holder and the plastic sleeve need to be fixed by dispensing glue, the operation is relatively difficult in an actual production process and a yield rate is low.

SUMMARY

A technical problem to be resolved by the present invention is to provide an improved hemostatic clip.

To achieve the above purpose, the present invention uses the following technical solution:

A hemostatic clip includes an inner sleeve, a transitional inner sleeve, a clip holder, a ball head pull rod, a plurality of steel micro balls, and two clip arms, where the ball head pull rod is accommodated in the transitional inner sleeve, the transitional inner sleeve is accommodated in the inner sleeve, the inner sleeve is limited between the transitional inner sleeve and the clip holder, and the steel micro balls are clamped between the clip holder and the transitional inner sleeve.

The steel micro balls are fixed to the clip holder. By pulling the ball head pull rod, the transitional inner sleeve is driven to move backward, so that a front end of the transitional inner sleeve is elastically deformed, to separate the transitional inner sleeve from the steel micro balls and the clip holder.

Preferably, the clip holder is provided with holes, the steel micro balls are fixed to the holes, and the steel micro balls protrude from an inner wall of the clip holder.

In a preferred embodiment provided by the present invention, the transitional inner sleeve includes a groove, and the groove is disposed at an upper end of the transitional inner sleeve, for accommodating the steel micro balls together with the holes.

Preferably, the ball head pull rod includes a ball head, a pull rod, a first connecting tube, and a second connecting tube arranged coaxially, the ball head is disposed at an upper end of the pull rod, and the ball head is connected to the clip arms; a lower end of the pull rod is connected to an upper end of the first connecting tube, and a lower end of the first connecting tube is inserted into an upper end of the second connecting tube; and the first connecting tube is disposed inside the transitional inner sleeve, and the second connecting tube is disposed outside a lower end of the transitional inner sleeve.

In another preferred embodiment provided by the present invention, the transitional inner sleeve includes a plurality of hemispherical concaves, and the hemispherical concaves are arranged at the upper end of the transitional inner sleeve, for accommodating the steel micro balls together with the holes.

Preferably, the ball head pull rod includes a ball head, a pull rod, a first connecting tube, a second connecting tube, and a rotation portion arranged coaxially, the ball head is disposed at an upper end of the pull rod, and the boll head is connected to the clip anus: a lower end of the pull rod is connected to an upper end of the first connecting tube, and a rotation portion is disposed between the first connecting tube and the second connecting tube.

A lower end of the transitional inner sleeve is fixedly provided with a rotary gasket, the rotary gasket includes a connecting slot, a shape of the connecting slot matches a shape and a size of the rotation portion, and the shape of the rotation portion allows the ball head pull rod to move freely along an axial direction in the transitional inner sleeve, and causes the ball head pull rod to drive the transitional inner sleeve to rotate when rotating.

Preferably, a cross section of the rotation portion is non-circular, and a maximum radial size of the rotation portion is less than inner diameters of the first connecting tube and the second connecting tube.

The rotary gasket includes a non-circular connecting slot for connecting to a non-circular part of a cross section of a middle portion of the pull rod.

Preferably, the inner sleeve is a three-section sleeve large in the middle and small at two ends, an outer diameter of an upper end of the inner sleeve and an outer diameter of a lower end of the inner sleeve are both less than an outer diameter of a middle portion, and the upper end of the inner sleeve is inserted into the clip holder.

Preferably, the lower end of the transitional inner sleeve is provided with a lug boss, and an outer diameter of the lug boss is equal to the outer diameter of the lower end of the inner sleeve.

Preferably, the hemostatic clip further includes a spring tube, a cable, and a control handle, the lower end of the inner sleeve is connected to the spring tube, an upper end of the cable is connected to a lower end of the ball head pull rod, and a lower end of the cable and a lower end of the spring tube are connected to the control handle.

The hemostatic clip provided by the present invention implements the connection between the clip holder and the transitional inner sleeve by using the steel micro balls, and the separation of the transitional inner sleeve from the steel, micro balls and the clip holder by pulling the cable to cause the front end of the transitional inner sleeve to be elastically deformed. During assembling, the steel micro balls are fixed with the clip holder and then assembled with the front end of the transitional inner sleeve, to implement the connection between the clip holder and the transitional inner sleeve. The structure is simple, the assembly is convenient, and the operation is easy and highly reliable.

DETAILED DESCRIPTION

Figure 1:
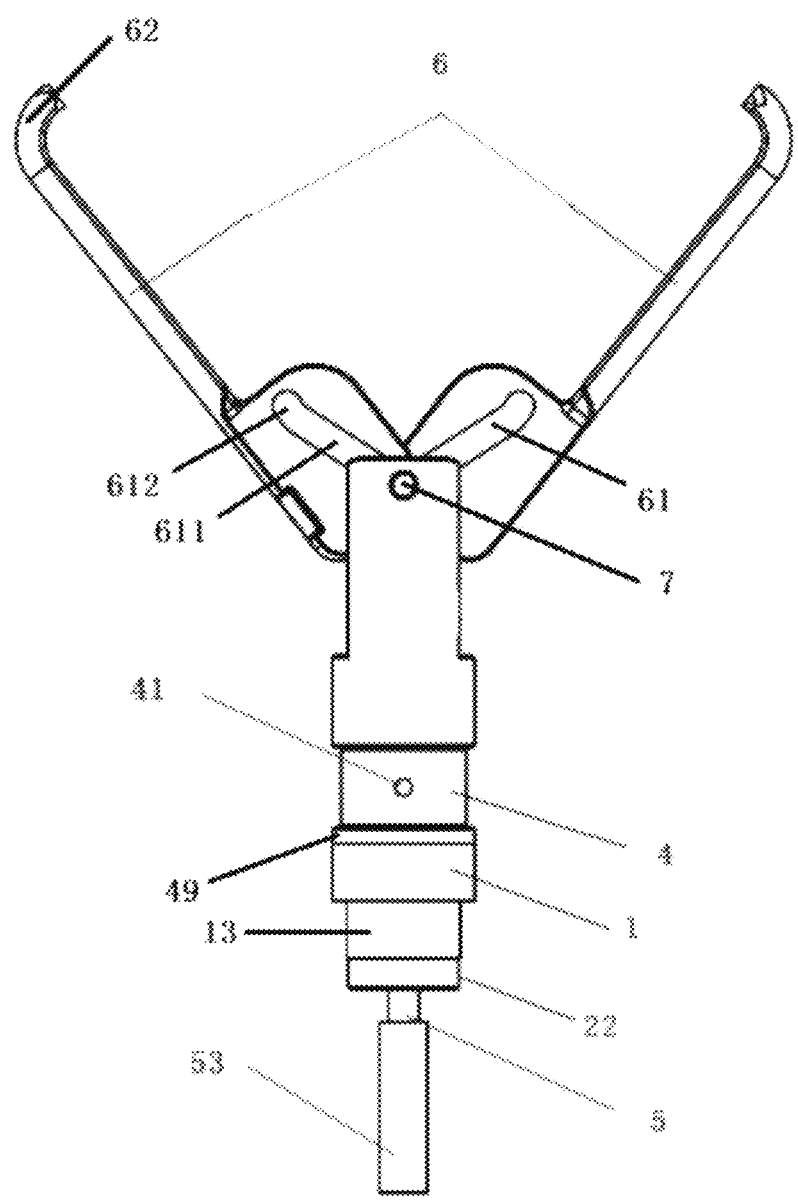
FIG. 1 is a cross-sectional view of a hemostatic clip in an open state according to Embodiment 1 of the present invention.

The following further describes the technical solutions of the present invention with reference to the accompanying drawings and specific embodiments.

Embodiment 1

As shown in FIG. 1 to FIG. 4, Embodiment 1 of the present invention discloses a hemostatic clip, including an inner sleeve 1, a transitional inner sleeve 2, a plurality of steel micro balls 3, a clip holder 4, a ball head pull rod 5, two clip arms 6, and a fixing pin shaft 7. The two clip arms 6 are disposed at a front end of the clip holder 4 through the fixing pin shaft 7, and lower ends of the two clip arms 6 are connected to au upper end of the ball head pull rod 5. The ball head pull rod 5 is accommodated in the transitional inner sleeve 2, the transitional inner sleeve 2 is accommodated in the inner sleeve 1, and the inner sleeve 1 is limited between the transitional inner sleeve 2 and the clip holder 4. The steel, micro balls 3 are clamped between the clip holder 4 and the transitional inner sleeve 2, the steel micro balls 3 are embedded in an inner wall of the clip holder 4 and fixedly connected to the clip holder 4, and the steel micro balls 3 are also embedded in an outer wall of a front end of the transitional inner sleeve 2, for implementing connection between the clip holder 4 and the transitional inner sleeve 2.

Figure 5:
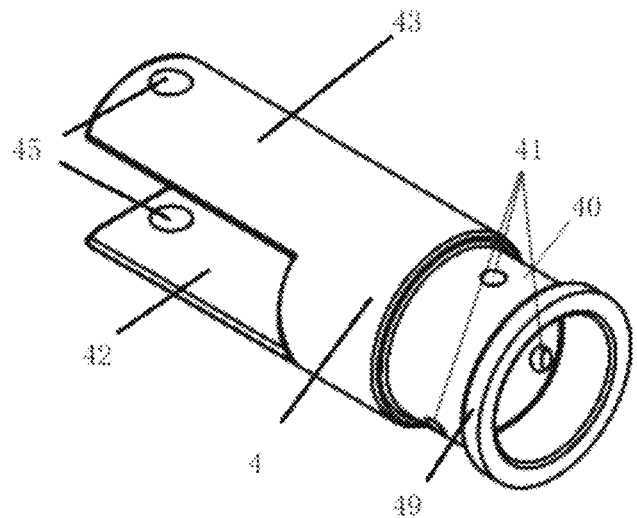
FIG. 5 is a schematic three-dimensional structural view of a transitional inner sleeve in the hemostatic clip according to Embodiment 1 of the present invention.
Figure 6:
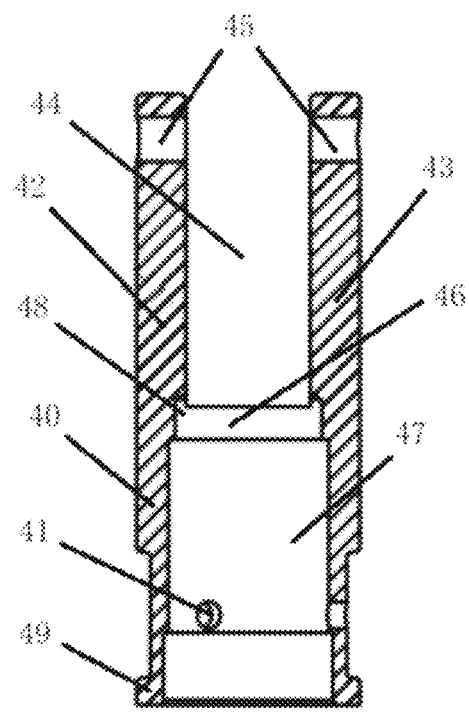
FIG. 6 is a schematic cross-sectional structural view of the transitional inner sleeve in FIG. 5.

As shown in FIG. 5 to FIG. 6, the clip holder 4 includes an integrally formed circular tube 40 and two supports 42 and 43 arranged above the circular tube 40. The support 42 and the support 43 are arranged opposite to each other, and a long slot 44 is formed between the two supports. Front ends of the support 42 and the support 43 are provided with through holes 45 correspondingly. An opening 46 is formed at a position where the circular tube 40 of the clip holder 4 meets the two supports 42 and 43. Below the opening 46 is a lumen 47 with a larger inner diameter. An aperture of the opening 46 is greater than a spacing between the two supports 42 and 43, and less than an inner diameter of the lumen 47, thereby forming an annular flange 48 at the position of the opening 46 to lock the clip arm 6.

Figure 2:
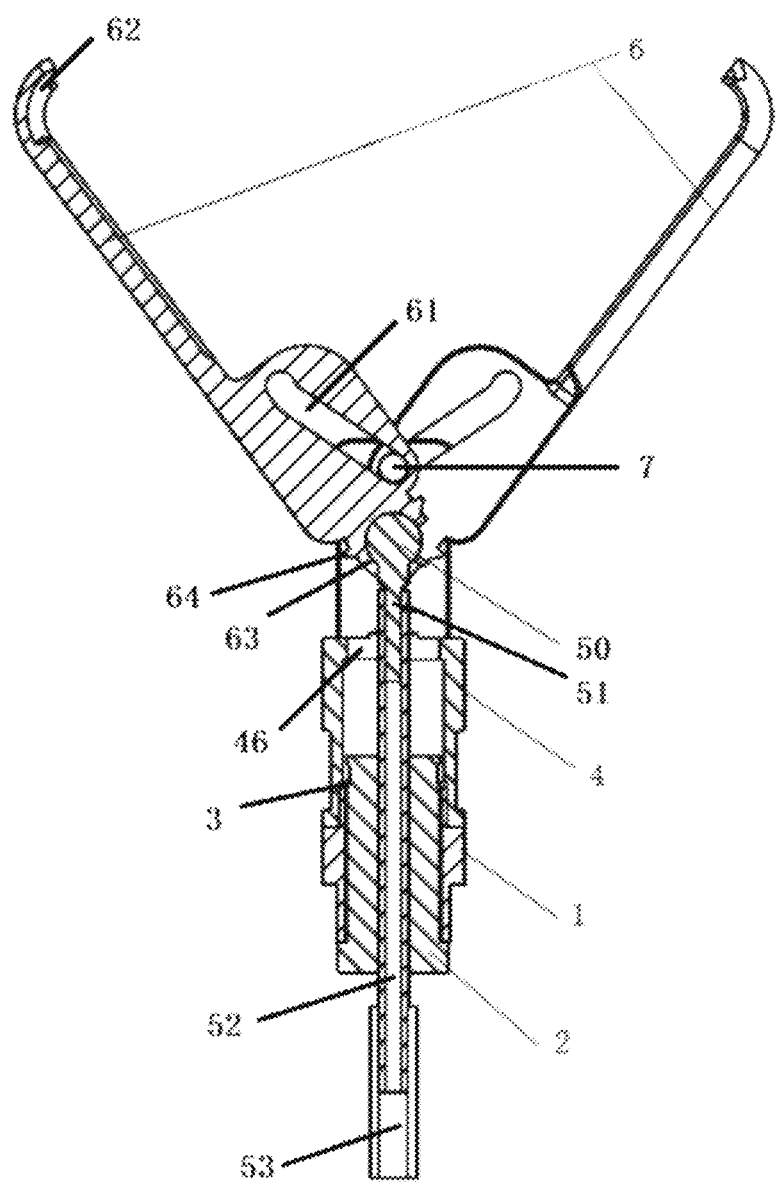
FIG. 2 is a schematic structural front view of the hemostatic clip in FIG. 1.

As shown in FIG. 1 and FIG. 2, the two clip arms 6 are disposed in the long slot 44 between the two supports 42 and 43 through the fixing pin shaft 7. The fixing pin shaft 7 passes through sliding slots 61 disposed in middle portions of the two clip arms 6 respectively, and two ends of the fixing pin shaft 7 are respectively fixed in the through holes 45 of the support 42 and the support 43.

The two clip arms 6 are arranged opposite to each other, a front end of the clip arm 6 is provided with a zigzag clamping portion 62, the middle portion of the clip arm 6 is provided with the elongated sliding slot 61, and the fixing pin shaft 7 may slide in the sliding slot 61. The sliding slot 61 includes an inclined portion 611 and a bent portion 612. The bent portion 612 is disposed at a position of the sliding slots 61 close to the front end of the clip arm 6. When the fixing pin shaft 7 moves to the bent portion 612, the two clip arms 6 are in closed and locked positions. A distance between the inclined portion 611 and an outer wall of the clip arm 6 gradually decreases in a direction from a rear end to a front end of the clip arm 6, and an extension direction of the bent portion 612 is parallel to a length direction of the clip arm 6.

The rear end of the clip arm 6 is provided with a hemispherical shell-shaped connecting portion 63 for connecting to a ball head 50 of the ball head pull rod 5. The ball head 50 of the ball head pull rod 5 is limited to the inside of the hemispherical shell-shaped connecting portion 63 of the two clip arms 6. By pulling down the ball head pull rod 5, the ball head 50 drives the connecting portion 63 to move downward, and the fixing pin shaft 7 slides along the sliding slot 61 disposed in the middle portion of the clip arm 6. Under the effect of the fixing pin shaft 7, the two clip arms 6 close and clip tissues. Before the fixing pin shaft 7 enters the bent portion 612, with a push-pull action of the ball head pull rod 5, the two clip arms 6 can be opened and closed repeatedly. When the fixing pin shaft 7 enters the bent portion 612, the two clip arms 6 are locked.

A protrusion 64 is provided on an outer wall of the connecting portion 63 of the clip arms 6 to cooperate with the annular flange 48 provided on an inner wall of the clip holder 4 to lock the clip arms 6. After the clamping portions 62 of the two clip anus 6 are clamped, by pulling down the closed clip arms 6, the protrusion 64 passes through an opening of the clip holder 4 and then is caught below the annular flange 48 in the clip holder 4, thereby locking the clip arms 6 in the clip holder 4.

A separation mechanism of the above hemostatic clip is described in further detail below with reference to FIG. 5 to FIG. 10.

As shown in FIG. 5 and FIG. 6, a lower end of the clip holder 4 has a protruded rib 49 for abutting against an upper shoulder 15 of the inner sleeve 1. Above the protruding ribs 49, a plurality of holes 41 are provided in a circumferential direction, and the steel micro balls 3 may be fixed in the holes 41. Preferably, there are two or more holes, which are evenly distributed on a circumference of the clip holder 4, the steel micro balls 3 are welded in the holes 41 and the steel micro balls 3 protrude from the inner wall of the clip holder 4 inward (that is, in a direction toward a central axis). More preferably, three holes 41 with 120-degree included angles are provided on the clip holder 4, for accommodating a part of a steel micro ball 3 respectively (that is, a part of the steel micro ball is inside the circular hole, and a part is exposed outside the circular hole and is accommodated in a groove 21 of the transitional inner sleeve 2). In an assembled state, the holes 41 and the groove 21 of the transitional inner sleeve 2 are aligned to accommodate the steel micro balls 3.

Figure 7:
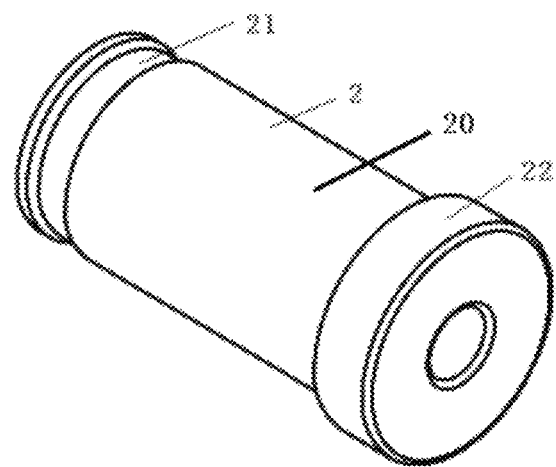
FIG. 7 is a schematic cross-sectional structural view of an inner sleeve in the hemostatic clip according to the present invention.
Figure 8:
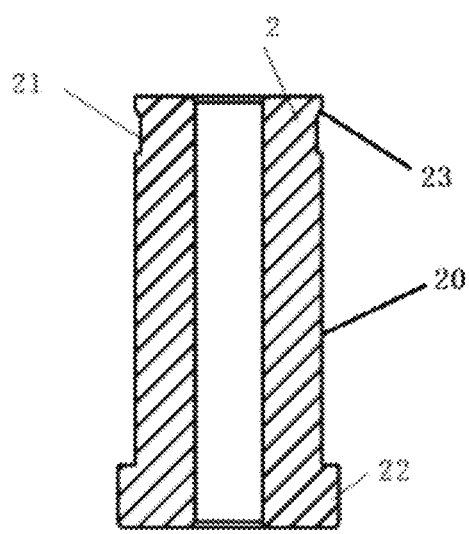
FIG. 8 is a schematic three-dimensional structural view of the inner sleeve in FIG. 7.

As shown in FIG. 7 and FIG. 8, the transitional inner sleeve 2 is shaped as a three-stage casing structure. The transitional inner sleeve 2 includes a hollow tube body 20, an upper end of the tube body 20 is provided with the groove 21, and a lower end of the tube body 20 is provided with a lug boss 22, so that in the assembled state, one end close to the clip arm 6 is used as the upper end, that is, one end shown as an upper end in FIG. 2 is used as the upper end. The tube body 20 of the transitional inner sleeve 2 has the same inner diameter. The upper end of the tube body 20 is provided with the groove 21 for accommodating parts of the steel micro balls 3. Moreover, preferably, an upper wall of the groove 21 is an inclined surface 23 (referring to FIG. 8), so that after an upper end of the transitional inner sleeve 2 is elastically deformed, the steel, micro balls 3 can be released from the groove 21. The lower end of the tube body 20 is provided with the lug boss 22, an outer diameter of the lug boss 22 is greater than an outer diameter of the tube body 20 of the transitional inner sleeve 2, and the outer diameter of the lug boss 22 is equal to an outer diameter of a lower end 13 of the inner sleeve 1.

Figure 9:
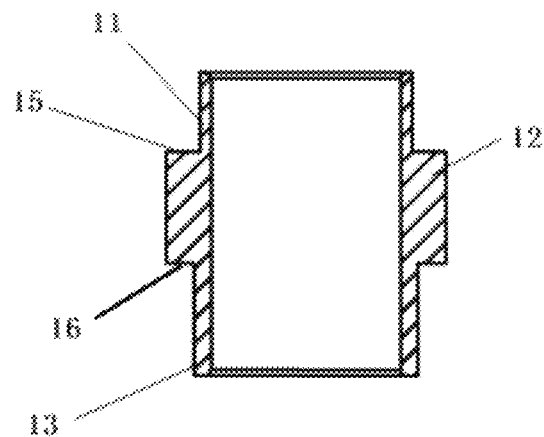
FIG. 9 is a schematic three-dimensional structural view diagram of a clip holder in the hemostatic clip according to the present invention.
Figure 10:
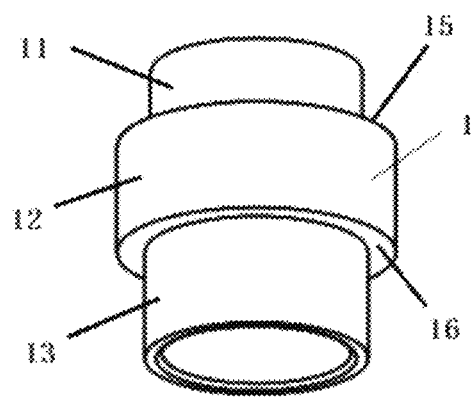
FIG. 10 is a schematic cross-sectional structural view of the clip holder in FIG. 9.

As shown in FIG. 9 and FIG. 10, the inner sleeve 1 is a hollow tubular structure, and the inner sleeve 1 is a three-section sleeve, which has larger middle portion and two smaller ends, including an upper end 11, a middle portion 12 and a lower end 13. The inner sleeve 1 has the same inner diameter as a whole, and an inner wall of the inner sleeve 1 is in contact with an outer wall of the tube body 20 of the transitional inner sleeve 2. The middle portion 12 of the inner sleeve 1 has the largest outer diameter, an outer diameter of the upper end 11 of the inner sleeve 1 and an outer diameter of the lower end 13 of the inner sleeve 1 are both less than the outer diameter of the middle portion 12. The outer diameter of the middle portion 12 of the inner sleeve is approximately the same as a maximum outer diameter of the clip holder 4. The upper shoulder 15 is formed at a position where the middle portion 12 of the inner sleeve 1 meets the upper end 11 of the inner sleeve 1, and a lower shoulder 16 is formed at a position where the middle portion 12 of the inner sleeve 1 meets the lower end 13 of the inner sleeve 1. The upper end 11 of the inner, sleeve 1 is inserted into the clip holder 4, and a lower end face of the protruded rib 49 of the clip holder 4 abuts against the upper shoulder 15 of the inner sleeve 1. The lower end 13 of the inner sleeve 1 is inserted into a spring tube 8, a part below the lower shoulder 16 of the inner sleeve 1 is fixedly connected to the spring tube 8 of the hemostatic clip (referring to FIG. 11), and a back end of the spring tube 8 is fixed to a control handle 9. In addition, the lower end 13 of the inner sleeve 1 abuts against the lug boss 22 of the transitional inner sleeve 2, so that the lower end 13 of the inner sleeve 1, has a limiting effect on an upward movement of the transitional inner sleeve 2, and limits the inner sleeve 1 between the protruded rib 49 of the clip holder 4 and the lug boss 22 of the transitional inner sleeve 2. The outer diameter of the lower end 13 of the inner sleeve 1 is the same as the outer diameter of the lug boss 22 of the transitional inner sleeve 2.

Figure 3:
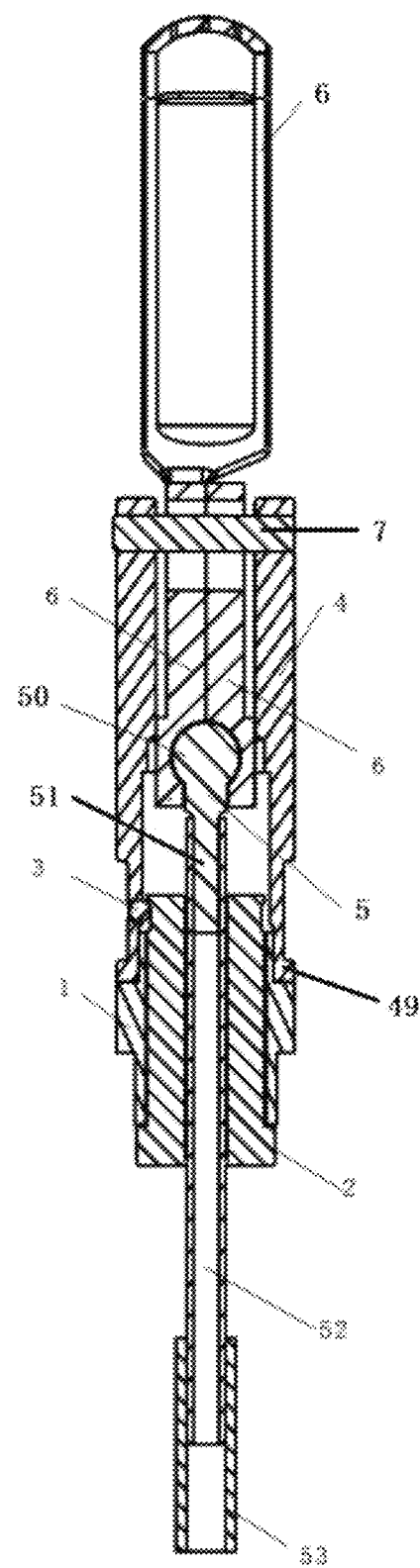
FIG. 3 is a cross-sectional view of the hemostatic clip in a closed state according to Embodiment 1 of the present invention.

According to the above embodiment, further, as shown in FIG. 2 and FIG. 3, the ball head pull rod 5 includes a ball head 50, a pull rod 51, a first connecting tube 52, and a second connecting tube 53 arranged coaxially from top to bottom. The ball head 50 is disposed at an upper end of the pull rod 51, the ball head 50 and the pull rod 51 may be integrally formed, a lower end of the pull rod 51 is inserted and fixed into an upper end of the first connecting tube 52, and a lower end of the first connecting tube 52 is inserted and fixed into an upper end of the second connecting tube 53. For ease of assembly, the ball head 50, the pull rod 51, the first connecting tube 52, and the second connecting tube 53 are detachable and may be fixedly connected together by interference fit or by welding or gluing, or certainly may be integrally formed. The ball head 50 is connected to the clip arms 6 of the hemostatic clip. The first connecting tube 52 is disposed inside the transitional inner sleeve 2, and the second connecting tube 53 is disposed outside the lower end of the transitional inner sleeve 2 for connecting to a cable, thereby implementing a push-pull action through the control handle.

Figure 11:
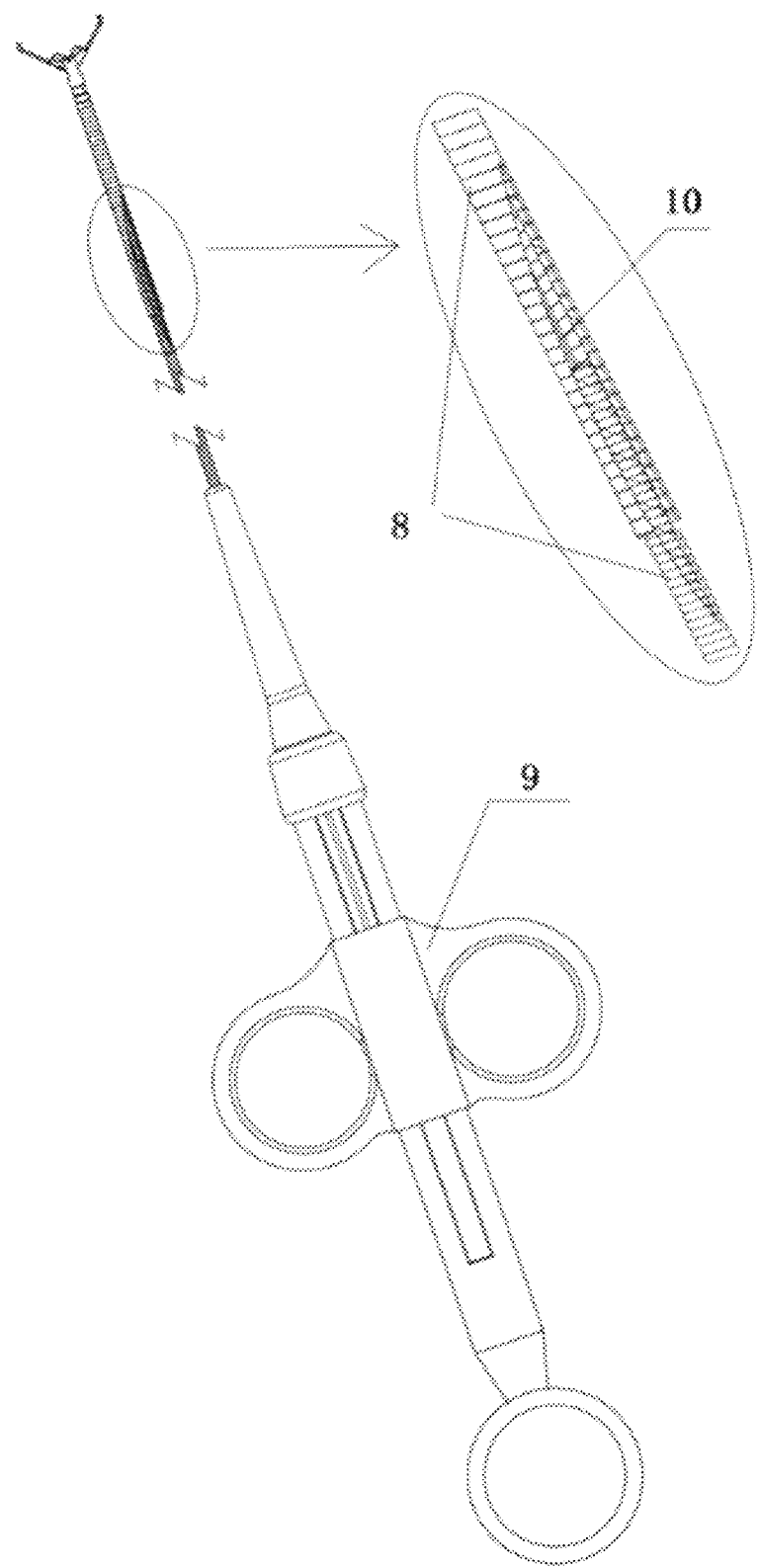
FIG. 11 is a schematic overall structural view of the hemostatic clip according to the present invention.

In this embodiment, to adapt to the fixation of a small-size clamp head and the cable, a first connecting tube 52 with a smaller outer diameter and a second connecting tube 53 with a larger outer diameter are disposed in the ball head pull rod 5, for fixing front ends of the ball head pull rod 5 and the cable 10 (referring to FIG. 11). The cable 10 extends backward from the spring tube 8, and a back end of the cable 10 is fixed to the control handle 9. An outer diameter of the pull rod 51 matches art inner diameter of the first connecting tube 52, an outer diameter of the first connecting tube 52 may match an inner diameter of the transitional inner sleeve 2 and an inner diameter of the second connecting tube 53, and the inner diameter of the second connecting tube 53 matches an outer diameter of the cable.

Figure 4:
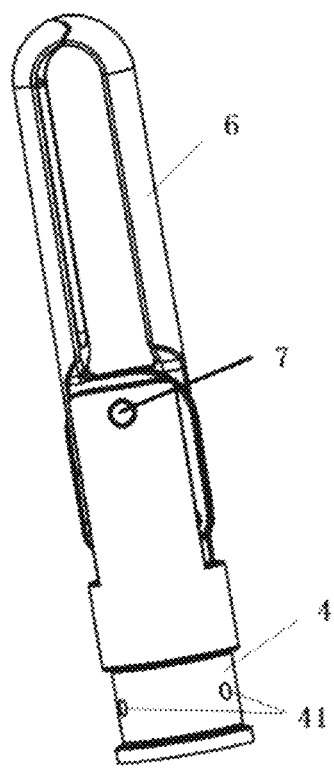
FIG. 4 is a schematic state view of the hemostatic clip in FIG. 3 after separation.
Figure 4:
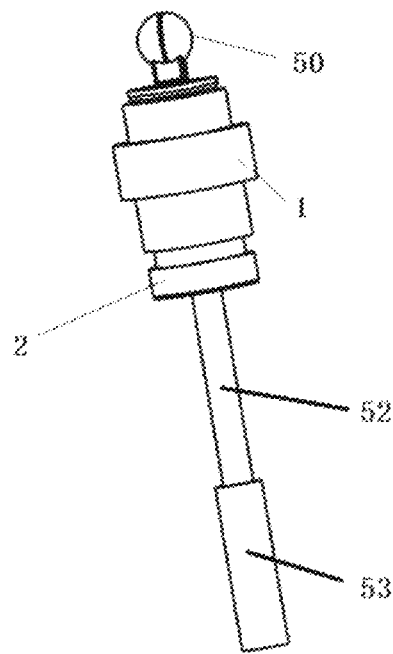

As shown in FIG. 2 to FIG. 4, a diameter of the ball head 50 is greater than a diameter of an inner hole of the transitional inner sleeve 2. When a traction is performed on the ball head pull rod 5 by pulling, after the ball head 50 of the ball head pull rod 5 is separated from the clip arms 6, because the diameter of the ball head 50 is greater than the diameter of the inner hole of the transitional inner sleeve 2, the transitional inner sleeve 2 may be driven to move downward when the ball head pull rod 5 is pulled with a continued force.

When the transitional inner sleeve 2 moves downward, a part of the upper end of the transitional inner sleeve 2 above the slot 21 is elastically deformed, and parts of the steel micro balls 3 accommodated in the groove 21 slightly move in a radial direction along an inclined upper wall 23, that is, a direction away from a central axis. The steel micro balls 3 move in the radial direction until reaching beyond the upper wall 23 (that is, out of the groove 21). In this case, the transitional inner sleeve 2 is separated from the steel micro balls 3, further causing the transitional inner sleeve 2 to be separated from the clip holder 4. After the transitional inner sleeve 2 is separated from the clip holder 4, the transitional inner sleeve 2 continues to move downward under the traction of the pull rod 53. The inner sleeve 1 and the spring tube 8 are then separated from the clip holder 4, thereby separating the hemostatic clip.

Embodiment 2

A structure different from that in Embodiment 1 in this embodiment is described below with reference to the accompanying drawings, and the same structure is not repeated.

Figure 12:
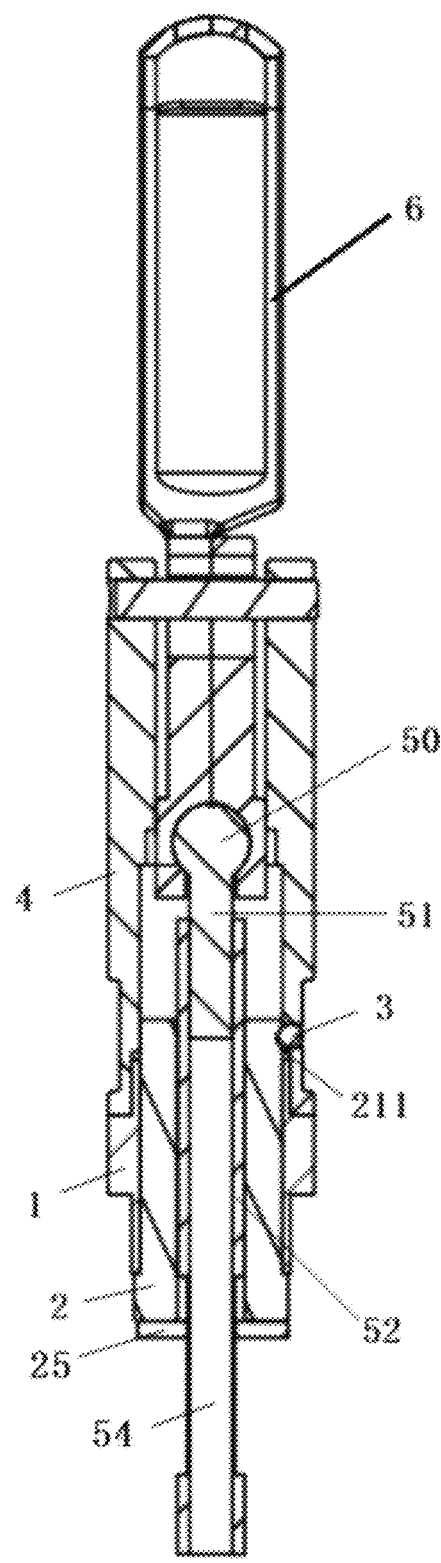
FIG. 12 is a schematic cross-sectional structural view of a hemostatic clip in a closed state according to Embodiment 2 of the present invention.
Figure 13:
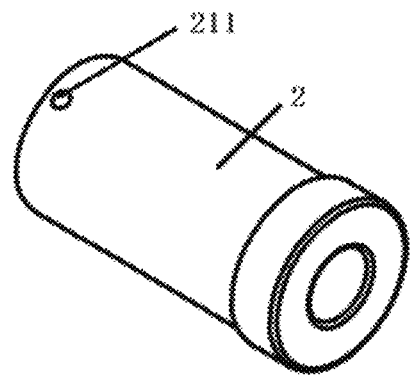
FIG. 13 is a schematic three-dimensional structural view diagram of a transitional inner sleeve according to Embodiment 2 of the present invention.

In this embodiment, as shown in FIG. 12 and FIG. 13, the transitional inner sleeve 2 is improved in structure, so that the transitional inner sleeve 2 and the clip holder 4 are relatively fixed in position, and the transitional inner sleeve 2 cannot rotate relative to the clip holder 4. Specifically in this embodiment, the upper end of the transitional inner sleeve 2 is provided with hemispherical concaves 211 to replace the groove 21 in Embodiment 1. When the transitional inner sleeve 2 and the clip holder 4 are assembled, parts of steel micro, balls 3 are fixed in through holes 41 of the clip holder 4, for example, by welding; and the other parts of the steel micro balls 3 are exposed outside the through holes 41 and contained in the hemispherical concaves 211. That is, the through holes 41 are aligned with the concaves 211 to accommodate the steel micro balls 3 together.

In this embodiment, the ball head pull rod 5 is also improved in structure, and a rotary gasket 25 is added to a lower end of the transitional inner sleeve 2, so that the ball head pull rod 5 may drive the transitional inner sleeve 2 through the rotary gasket 25, to further drive the clip holder 4 and the clip arms 6 to perform a 360° rotation relative to the inner sleeve 1.

Figure 14:
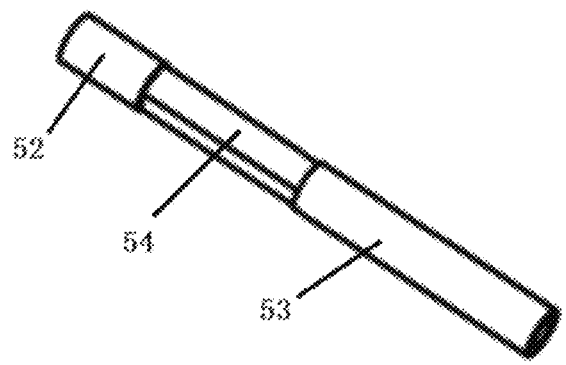
FIG. 14 is a schematic three-dimensional structural view of a pull rod according to Embodiment 2 of the present invention.
Figure 15:
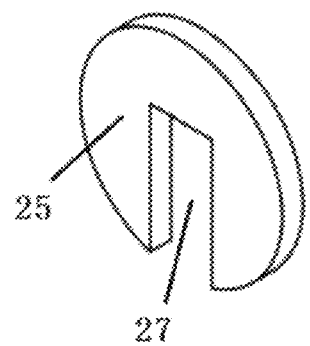
FIG. 15 is a schematic three-dimensional structural view of a rotary gasket according to Embodiment 2 of the present invention.

As shown in FIG. 12 and FIG. 14, the ball head pull rod 5 includes a ball head 50, a pull rod 51, a first connecting tube 52, a second connecting tube 53, and a rotation portion 54. The rotation portion 54 with a rectangular cross section (non-circular cross section) is added between the first connecting tube 52 and the second connecting tube 53. Inner diameters of the first connecting tube 52 and the second connecting tube 53 are the same. A maximum radial size of the rotation portion 54 (the maximum cross section of the rotation portion 54) is less than the inner diameter of the first connecting tube 52, that is, less than an inner diameter of the transitional inner sleeve 2, and is also less than an outer diameter of the second connecting tube 53. The lower end (one end away from the ball head 50) of the transitional inner sleeve 2 is fixed to the rotary gasket 25 shown in FIG. 15, and a rectangular connecting slot 27 is provided in the rotary gasket 25. A shape and a size of the rectangular connecting slot 27 in the rotary gasket 25 match those of the rotation portion 54, and the size of the connecting slot 27 is less than outer diameters of the first connecting tube 52 and the second connecting tube 53, thereby allowing the rotation portion 54 to move in an up and down direction (that is, an axial direction of the ball head pull rod 5) within the rectangular connecting slot 27, and the rotation portion 54 can only move in a radial direction of the ball head pull rod 5 together with the rotary gasket 25. In other words, the rotation portion is configured to allow the hall head pull rod to move freely and axially along the transitional inner sleeve, and cause the transitional inner sleeve to rotate with the ball head pull rod rotating.

A person of ordinary skill in the art may understand that in Embodiment 2, the connecting slot 27 on the rotary gasket 25 may have other shapes and is not limited to a rectangle, for example, may be a star shape or an ellipse shape. Correspondingly, a shape of the cross section of the rotation portion 54 of the ball head pull rod 5 is also not limited to a rectangle, but only needs to meet: matching the shape of the connecting slot 27 and allowing the ball head pull rod 5 to move freely along an axial direction in the transitional inner sleeve 2, and causing the ball head pull rod 5 to drive the transitional inner sleeve 2 to rotate when rotating.

In actual use, when the ball head pull, rod 5 rotates, the rotary gasket 25 is fixedly connected to the transitional inner sleeve 2 and the rotary gasket 25 is clamped on the rotation portion 54. Therefore, the rotary gasket 25 rotates with the rotation portion 54. At the same time, the rotary gasket 25 drives the transitional inner sleeve 2 to rotate. The steel micro balls 3 on the transitional inner sleeve 2 then moves in a circumferential direction. In this embodiment, a front end of the transitional inner sleeve 2 is not provided with a groove to cooperate with the steel micro balls 3, but three concaves 211 to limit the steel micro balls 3, thereby driving the clip holder 4 and the clip arms 6 to rotate together when rotating the transitional inner sleeve 2.

Similar to Embodiment 1, when the clip holder 4 needs to be separated, by pulling down the ball head pull rod 5, the upper end of the transitional inner sleeve 2 is elastically deformed, and the steel micro balls 3 slide out of the concaves 211. Then, components such as the ball head pull rod 5, the transitional inner sleeve 2, the inner sleeve 1, the cable, and the spring tube are pulled out from the clip holder 4 to implement separation.

In the above two embodiments, a front end of the spring tube 8 is fixed to the inner sleeve 1, and a front end of the inner sleeve 1 is inserted into the clip holder 4. There is no fixing or limiting effect between the inner sleeve 1 and the clip holder 4. Therefore, during rotation of the clip holder 4, neither the spring tube 8 nor the inner sleeve 1 rotates.

In conclusion, the hemostatic clip provided by the present invention uses the steel micro balls to cooperate with the groove or the through holes to implement connection and separation of the clip holder and the transitional inner sleeve, and has a simple structure. Moreover, by simply pulling or rotating the pull rod, the opening, closing, and separation of the hemostatic clip can be implemented, which is easy to operate and highly reliable.

The hemostatic clip provided by the present invention is described in detail above. For a person of ordinary skill in the art, any obvious modifications made to the present invention without departing from the essence of the present invention will constitute an infringement of patent rights of the present invention, and corresponding legal liabilities will be born.

What is claimed is:

1. A hemostatic clip, comprising an inner sleeve, a transitional inner sleeve, a clip holder, a ball head pull rod, a plurality of steel micro balls, and two clip arms, wherein the ball head pull rod is accommodated in the transitional inner sleeve, the transitional inner sleeve is accommodated in the inner sleeve, the inner sleeve is limited between the transitional inner sleeve and the clip holder, the steel micro balls are clamped between the clip holder and the transitional inner sleeve, and the steel micro balls are mounted to the clip holder;

the ball head pull rod comprises a ball head, a pull rod, a first connecting tube, a second connecting tube, and a rotation portion that are arranged coaxially, the ball head is disposed at an upper end of the pull rod, and the ball head is connected to clamps; a lower end of the pull rod is connected to an upper end of the first connecting tube, and the rotation portion is disposed between the first connecting tube and the second connecting tube;

the rotation portion is configured to allow the ball head pull rod to move freely and axially along the transitional inner sleeve, and cause the transitional inner sleeve to rotate with the ball head pull rod rotating; and by pulling the ball head pull rod, the transitional inner sleeve is driven to move backward, so that a front end of the transitional inner sleeve is elastically deformed, to separate the transitional inner sleeve from the steel micro balls and the clip holder.

2. The hemostatic clip according to claim 1, wherein:
the clip holder is provided with holes, the steel micro balls are accommodated in the holes, and the steel micro balls protrude from an inner wall of the clip holder.

3. The hemostatic clip according to claim 2, wherein:
the transitional inner sleeve comprises a groove, and the groove is disposed at an upper end of the transitional inner sleeve for accommodating the steel micro balls together with the holes.

4. The hemostatic clip according to claim 2, wherein:
the transitional inner sleeve comprises a plurality of hemispherical concaves, and the hemispherical concaves are arranged at the upper end of the transitional inner sleeve, for accommodating the steel micro balls together with the holes.

5. The hemostatic clip according to claim 1, wherein:
a lower end of the transitional inner sleeve is fixedly provided with a rotary gasket, the rotary gasket comprises a connecting slot, the connecting slot matches the rotation portion.

6. The hemostatic clip according to claim 1, wherein:
the rotation portion is of a non-circular cross section, and a maximum radial size of the rotation portion is less than inner diameters of the first connecting tube and the second connecting tube; and
the rotary gasket comprises a non-circular connecting slot for connecting to the rotation portion of the non-circular cross section.

7. The hemostatic clip according to claim 1, wherein:
the inner sleeve is a three-section sleeve which has a larger middle portion and two smaller ends, an outer diameter of an upper end of the inner sleeve and an outer diameter of a lower end of the inner sleeve are both less than an outer diameter of the middle portion, and the upper end of the inner sleeve is inserted into the clip holder.

8. The hemostatic clip according to claim 7, wherein:
a lower end of the transitional inner sleeve is provided with a lug boss, and an outer diameter of the lug boss is equal to the outer diameter of the lower end of the inner sleeve.

9. The hemostatic clip according to claim 7, further comprising a spring tube, a cable, and a control handle, the lower end of the inner sleeve is connected to the spring tube, an upper end of the cable is connected to a lower end of the ball head pull rod, and a lower end of the cable and a lower end of the spring tube are connected to the control handle.

* * * * *